(12) United States Patent
Enzerink et al.

(10) Patent No.: US 7,918,809 B2
(45) Date of Patent: *Apr. 5, 2011

(54) ORTHOPAEDIC BRACE HAVING A RANGE OF MOTION HINGE WITH AN ADJUSTABLE-LENGTH STRUT

(75) Inventors: Robert-Jan Enzerink, Davis, CA (US); James Gregory Finkes, Patterson, CA (US); Jeffrey Lee Telles, Tracy, CA (US)

(73) Assignee: Djo, LLC, Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/135,802

(22) Filed: Jun. 9, 2008

(65) Prior Publication Data

US 2008/0306421 A1    Dec. 11, 2008

Related U.S. Application Data

(63) Continuation of application No. 11/510,408, filed on Aug. 25, 2006, now Pat. No. 7,384,406, which is a continuation of application No. 10/141,494, filed on May 7, 2002, now Pat. No. 7,097,627, which is a continuation of application No. 09/608,940, filed on Jun. 30, 2000, now Pat. No. 6,383,156.

(60) Provisional application No. 60/156,342, filed on Sep. 27, 1999.

(51) Int. Cl.
  *A61F 5/00* (2006.01)
(52) U.S. Cl. ............................................. 602/16; 602/26
(58) Field of Classification Search ................ 602/5, 16, 602/19–23, 26–27; 128/878–879, 882
See application file for complete search history.

(56) References Cited

U.S. PATENT DOCUMENTS

| 431,797 | A |   | 7/1890 | Blattmachr |       |
|---------|---|---|--------|------------|-------|
| 552,143 | A |   | 12/1895 | Rankin    |       |
| 575,199 | A |   | 1/1897 | Autenrieth |       |
| 649,237 | A | * | 5/1900 | Dyson ............................. | 602/16 |
| 932,177 | A |   | 8/1909 | Roth       |       |
| 1,018,452 | A |   | 2/1912 | Slaughter |       |
| 1,336,695 | A | * | 4/1920 | Gromes ......................... | 602/16 |
| 1,559,339 | A |   | 10/1925 | Masland  |       |
| 1,780,959 | A |   | 11/1930 | Wilkes    |       |
| 2,654,365 | A |   | 10/1953 | Whitaker  |       |
| 2,832,334 | A |   | 4/1958 | Whitelaw  |       |
| 3,805,773 | A |   | 4/1974 | Sichau    |       |
| 3,913,570 | A |   | 10/1975 | Madden et al. |   |
| 4,436,099 | A |   | 3/1984 | Raftopoulos |     |
| 4,481,941 | A |   | 11/1984 | Rolfes   |       |

(Continued)

FOREIGN PATENT DOCUMENTS

DE           367369        1/1923

(Continued)

*Primary Examiner* — Michael A. Brown
(74) *Attorney, Agent, or Firm* — Ropes & Gray LLP

(57) ABSTRACT

An orthopaedic brace includes a strut length adjustment assembly to change the operable length of the strut for sizing the brace on a patient without the need for special tools or cutting of the strut. The adjustment assembly includes a biased adjustment mechanism that coacts with a plurality of notches in the strut to variably set/position the strut relative to the adjustment assembly to set the struts length. Each upper and lower strut preferably includes a strut length adjustment assembly to independently set the length of each strut. The strut length adjustment assembly retains a strut and includes a strap retention mechanism that is configured to releasably engage the strap.

21 Claims, 4 Drawing Sheets

U.S. PATENT DOCUMENTS

| | | |
|---|---|---|
| 4,524,766 A | 6/1985 | Petersen |
| 4,572,170 A | 2/1986 | Cronk et al. |
| 4,751,920 A | 6/1988 | Mauldin et al. |
| 4,768,500 A | 9/1988 | Mason et al. |
| 4,776,326 A | 10/1988 | Young et al. |
| 4,817,588 A | 4/1989 | Bledsoe |
| 4,982,732 A | 1/1991 | Morris |
| 5,018,514 A | 5/1991 | Grood et al. |
| 5,025,782 A | 6/1991 | Salerno |
| 5,033,461 A | 7/1991 | Young et al. |
| 5,052,379 A | 10/1991 | Airy et al. |
| 5,063,917 A | 11/1991 | Young et al. |
| 5,138,911 A | 8/1992 | Lan |
| 5,383,844 A | 1/1995 | Munoz et al. |
| 5,421,810 A * | 6/1995 | Davis et al. .................. 602/16 |
| 5,437,619 A * | 8/1995 | Malewicz et al. ............ 602/20 |
| 5,547,464 A | 8/1996 | Luttrell et al. |
| 5,571,078 A | 11/1996 | Malewicz |
| 5,645,524 A | 7/1997 | Doyle |
| 5,653,680 A | 8/1997 | Cruz |
| 5,658,241 A | 8/1997 | Deharde et al. |
| 5,716,336 A * | 2/1998 | Hines et al. .................. 602/27 |
| 5,921,946 A * | 7/1999 | Tillinghast et al. ........... 602/16 |
| 6,383,156 B1 * | 5/2002 | Enzerink et al. .............. 602/16 |
| D481,460 S | 10/2003 | Doty et al. |
| 6,821,261 B2 | 11/2004 | Doty et al. |
| 7,097,627 B2 * | 8/2006 | Enzerink et al. .............. 602/23 |
| 7,384,406 B2 * | 6/2008 | Enzerink et al. ............... 602/5 |

FOREIGN PATENT DOCUMENTS

| | | |
|---|---|---|
| EP | 0665160 | 8/1995 |
| FR | 730670 | 8/1932 |
| FR | 1324883 | 3/1963 |
| FR | 2414325 | 8/1979 |
| GB | 19736 | 11/1902 |

* cited by examiner

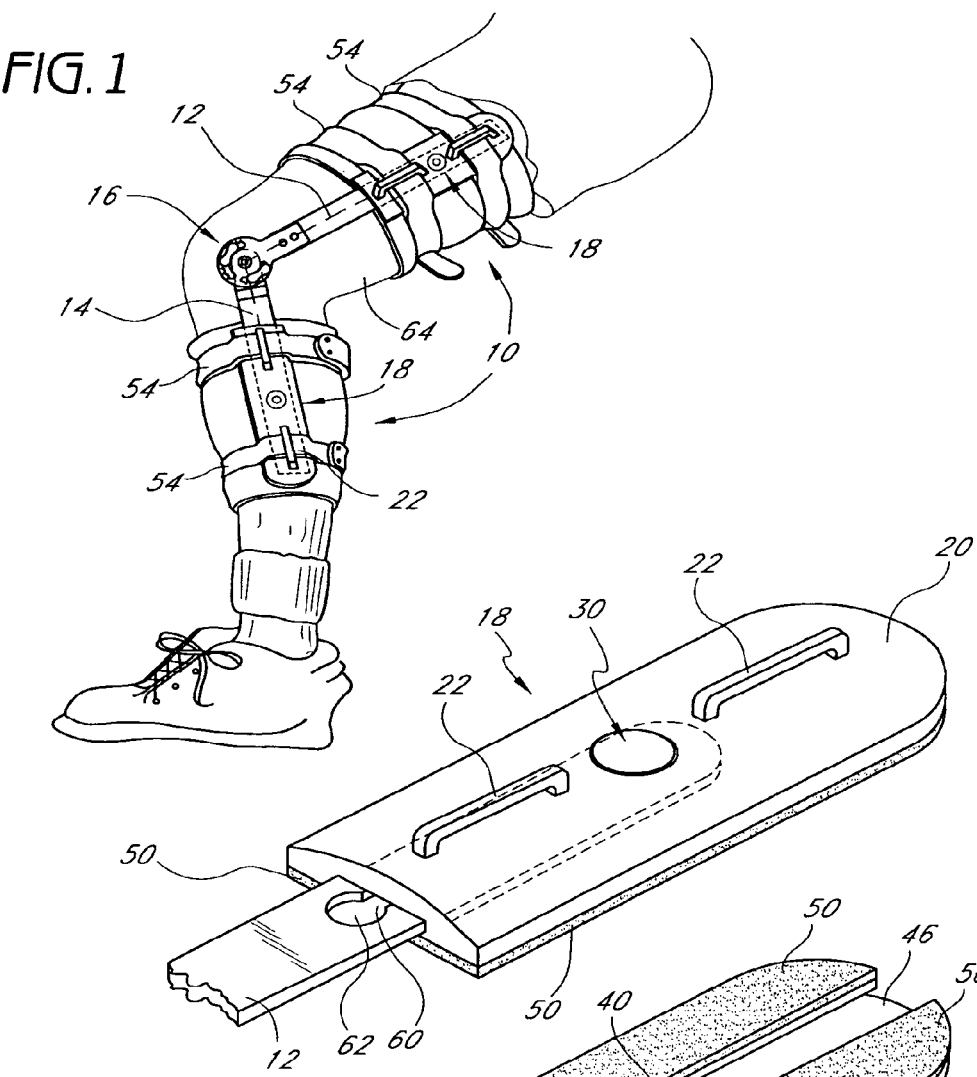
FIG.1
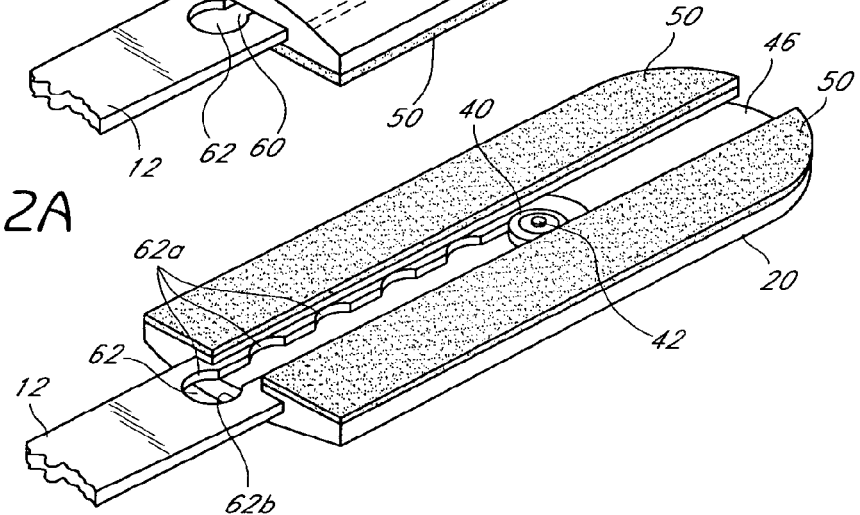
FIG.2A
FIG.2B

ORTHOPAEDIC BRACE HAVING A RANGE OF MOTION HINGE WITH AN ADJUSTABLE-LENGTH STRUT

CROSS-REFERENCE TO RELATED APPLICATIONS

This application is a continuation of U.S. application Ser. No. 11/510,408, filed on Aug. 25, 2006, which is a continuation of U.S. application Ser. No. 10/141,494, filed on May 7, 2002, now U.S. Pat. No. 7,097,627, which is a continuation of U.S. application Ser. No. 09/608,940, filed on Jun. 30, 2000, now U.S. Pat. No. 6,383,156, which claims the benefit of U.S. provisional application Ser. No. 60/156,342, filed on Sep. 27, 1999. Each of the priority applications is hereby incorporated by reference herein.

BACKGROUND OF THE INVENTION

1. Field of the Invention

The present application relates to orthopaedic braces adapted with an adjustable-length strut for use in stabilizing a joint after invasive surgery.

2. Description of the Related Art

In order to ensure the proper healing of a human joint after an injury or invasive surgery, it is often desirable to limit the pivotal motion of the human joint to a predetermined angular range between full extension and full flexion. The pivotal motion may be limited by a range of motion hinge disposed between an upper strut and a lower strut. In order for the orthopaedic brace to function properly, the struts must be adaptable to the body proportions of the patient.

The following U.S. patents, which describe orthopaedic braces of this general type, are herein incorporated by reference to establish the nature of such range of motion braces, and how and why such equipment is used. U.S. Pat. No. 552,143 issued on Dec. 31, 1895; U.S. Pat. No. 649,237 issued on May 8, 1900; U.S. Pat. No. 4,776,326 issued to Young et al., on Oct. 11, 1988 entitled "Modular Lower Limb Bracing System"; U.S. Pat. No. 4,817,588 issued to Bledsoe on Apr. 4, 1989 entitled "Motion Restraining Knee Brace"; U.S. Pat. No. 4,982,732 issued to Morris on Jan. 8, 1991 entitled "Orthopedic Rehabilitation Knee Brace"; U.S. Pat. No. 5,052,379 issued to Airy et al., on Oct. 1, 1991 entitled "Combination Brace and Wearable Exercise Apparatus for Body Joints"; and U.S. Pat. No. 5,018,514 issued to Grood et al., on May 28, 1991 entitled "Knee Brace".

It is well known that the orthopaedic braces described in the aforementioned incorporated patents suffer various problems, shortcomings and disadvantages. In some cases such braces cannot be adjusted to fit the patient, rather, the braces come in various fixed sizes. Alternatively, the braces are not easily adjustable, requiring, for example, tools to change the size of the struts. Some braces require actual cutting or breaking off pieces of the struts to permanently change the length of the struts. Others rely upon friction, as from a tightening screw, to less than positively lock the strut at the desire length.

It is thus an object of the present invention to provide an orthopaedic brace that is easy to adjust.

It is thus another object of the present invention to provide an orthopaedic brace that is adjustable without a need for tools.

It is thus further an object of the present invention to provide an orthopaedic brace that is adjustable without cutting or breaking a strut.

SUMMARY OF THE INVENTION

The present invention is an orthopaedic brace that has adjustable length struts.

In one form, the present invention is an orthopaedic brace including a first strut, a second strut, a hinge disposed between the first and second struts, and an adjustment assembly disposed on one of the first and second struts. The hinge is configured to allow movement of one of the first and second struts about an axis defined by the hinge. The adjustment assembly is configured to cooperate with the one of the first and second struts to adjustably set an operative length of the one of the first and second struts.

In another form, the present invention is an orthopaedic brace including an upper strut, a lower strut, a hinge disposed between the upper strut and the lower strut, and an adjustment assembly disposed on one of the first and second struts. The hinge is configured to allow movement of one of the upper and lower struts about an axis defined by the hinge. One of the upper and lower struts has a plurality of notches defining a plurality of strut length settings. The adjustment assembly is configured to cooperate with any one of the plurality of notches of the one of the first and second struts to selectively set a length of the one of the first and second struts.

In yet another form, the present invention is an orthopaedic brace including an upper strut, a lower strut, a hinge disposed between the upper strut and the lower strut, an upper adjustment assembly disposed on the upper strut, and a lower adjustment assembly disposed on the lower strut. The hinge is configured to allow movement of one of the upper and lower struts about an axis defined by the hinge. The upper adjustment assembly is configured to cooperate with the upper strut to adjustably set a length of the upper strut. The lower adjustment assembly is configured to cooperate with the lower strut to adjustably set a length of the lower strut.

Accordingly, the present invention improves upon the prior art by providing an orthopaedic brace strut that may be changed in length without the use of tools and with the ability to return to the original length, or some other length as desired.

The present invention also provides for a single-action positive lock for a strut length adjustment assembly rather than relying on friction. The ability to size and resize the struts provides a cost-effective and comfortable means to apply an orthopaedic brace to virtually any joint on the human body and eliminates the need to carry large inventories of braces that cannot be sized. By providing a positive lock, the improved brace also better protects the patient and speeds recovery.

The present invention also allows contoured wings, with cushioning material and/or non-slip material attached, to be used to limit movement of the brace after it has been attached and to provide increased comfort to the patient.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a side perspective view of an adjustable orthopaedic brace assembly having adjustable-length strut assemblies that embodies principles of the present invention showing the brace operatively connected to a human leg;

FIGS. 2A and 2B are, respectively, top and underside perspective views of an adjustable-length strut assembly for the orthopaedic brace of FIG. 1;

Corresponding reference characters indicate corresponding parts throughout the several views.

DETAILED DESCRIPTION OF THE PREFERRED EMBODIMENTS

Figure 3:
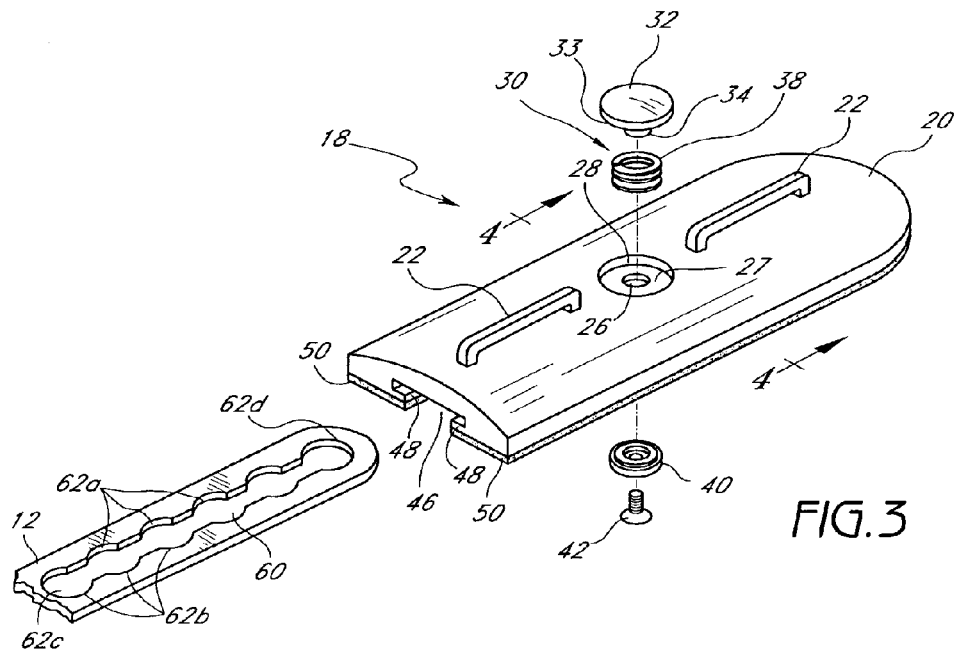
FIG. 3 is an exploded, perspective view of the adjustable-length strut assembly of FIGS. 2A and 2B.

An orthopaedic brace 10 is shown in FIG. 1 operatively attached to a leg 64 using a plurality of straps 54 mounted on an upper strut 12 and a lower strut 14 with a hinge assembly 16 disposed between the upper strut 12 and the lower strut 14. While only one side of the orthopaedic brace 10 is shown (i.e. the hinge assembly 16, the upper strut 12, and the lower strut 14 or "assembly") it should be understood that an identical, but mirror image, assembly is provided on the opposite side of the leg 64.

Each strut 12 and 14 is provided with a preferably identically configured wing assembly 18 although variations in either are contemplated, which is slidably mounted for adjustable movement on the elongated struts 12 and 14. Stated in another manner, each strut 12 and 14 is adjustable in length relative to the length of the strut between the hinge 16 and the straps 54 through adjustable strut assemblies 18. Such will be considered hereafter as the length adjustment of a strut. It should be appreciated that such assemblies 18 may be provided on both struts 12 and 14, or only on one of the two struts 12 and 14. As well, it should also be appreciated that adjustability of the length of a strut may be considered as either or both the adjustment of the assembly 18 relative to a strut (12 and/or 14), or as the adjustment of a strut (12 and/or 14) relative to the assembly 18.

The adjustable mounting of the wing assembly 18 on elongated struts 12 and 14 allows the struts to telescope or move in and out, one in opposition to the other, of the respective wing assembly 18, as will be described subsequently, to accommodate long or short legs, as one example, or long or short arms, as another example. Because the structure and function of the wing assembly is similar regardless of whether mounted to the upper strut 12 or the lower strut 14, reference will be made to only the upper strut 12 in the following description and its wing assembly 18. As well, because the structure and function of the struts 12 and 14 are identical (assuming each strut terminates in a wing assembly 18), reference to strut 12 in the following description will be construed to pertain to strut 14.

Referring to FIG. 2A, the wing assembly 18 has a wing body 20, which is preferably formed of a relatively rigid material, as for example plastic. The wing body 20 has an arcuate profile and is provided with one or more strap-retaining loops 22 for receiving the one or more adjustable straps 54 that are threaded through the loops 22 to encircle both the wing assembly 18 and a human limb, such as the leg 64 (as depicted in FIG. 1), thereby immovably securing the brace 10 to the leg 64, for example. FIG. 2B shows that the underside of the arcuate-shaped wing body 20 is provided with a generous layer of non-slip cushioning 50, both to pad the wearer's limb and to assure that the brace 10 remains in place.

FIGS. 2B, 3, 4A and 4B reveal that the underside of the wing body 20 defines a unitary channel 46 that runs longitudinally down the entire length the wing body 20. While the channel 46 is generally open, splitting the cushioning 50 into two halves, a lip 48 portion of the wing body 20 overhangs the channel 46 at each of the side edges of the channel 46 down the entire longitudinal length of each side of the channel 46. The channel 46 with opposing lips 48 receives the elongated strut 12 and retains and guides the strut 12 as it telescopes in and out of the channel 46. The open nature of the channel 46 also helps to reduce the overall weight of the orthopaedic brace 10.

Referring to FIGS. 2B and 3, the strut 12 has formed through its body a longitudinal slot 60. The length of the slot 60 may be varied depending upon the desired maximum and minimum lengths of the orthopaedic brace 10. Longitudinally spaced down each side of the slot 60 are a plurality of arcuate-shaped, stop notches generally designated 62. The notches 62 are equally divided into a plurality of notches 62a that are mirror images of, and directly across the slot 60 from, a plurality of opposing notches 62b, such that the opposing, arcuate-shaped pairs of notches 62a and 62b would define a circle if their ends were connected by an arc of constant radius equal to the distance from the center of the slot 60 to the center of the opposing notches. One end of the slot 60 contains an arcuate-shaped notch 62c and the other end of the slot 60 contains a mirror image arcuate-shaped notch 62d. Notches 62c and 62d are connected on each end to the outer ends of notches 62a and 62b. It should be appreciated that the notches may be shaped other than that shown.

Referring to FIG. 3, it can be seen that the wing body 20 also defines a depression or chamber 28 on the top of the body 20 which is shown as circular but can be any shape. The wing body 20 also defines an aperture 26 of smaller diameter than the chamber 28 that extends through the center of the chamber 28 all the way to the slot 60 on the underside of the wing body 20. The chamber 28 and aperture 26 are adapted to house a positive-lock, adjustment or button assembly 30.

The adjustment assembly 30 (FIG. 3) has a generally flat pushbutton top 32 that has a cylindrical extension 34 extending downward away from and perpendicular to the top. The cylindrical extension 34 has a radius that allows it to freely travel through the aperture 26 and the slot 60 without engaging any of the notches 62a and 62b. With additional reference to FIGS. 4A and 4B, a threaded aperture 36 extends down through the center of the top 32 and the extension 34 and is adapted to receive a screw 42 from the underside of wing body 20. Fitting over the extension 34 is a biasing spring 38 of smaller diameter than the chamber 26. A retaining bushing 40, with a radius approximating that of the notches 62a, 62b, 62c and 62d, is secured to the adjustment assembly 30 (extension 34) from the underside of the wing body 20 by the screw 42, which runs through the aperture 28 into the threaded aperture 36 in the extension 34 and thus the button 32. The spring 38 is thereby secured and sandwiched between the underside 33 of the top of the button 32 and a bottom 27 of the chamber 28.

Figure 4A:
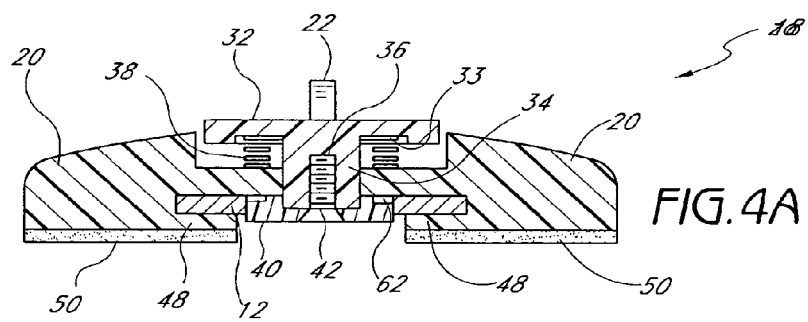
FIGS. 4A and 4B are cross-sectional views through the adjustable-length strut assembly taken along line 4-4 of FIG. 3.
Figure 4B:
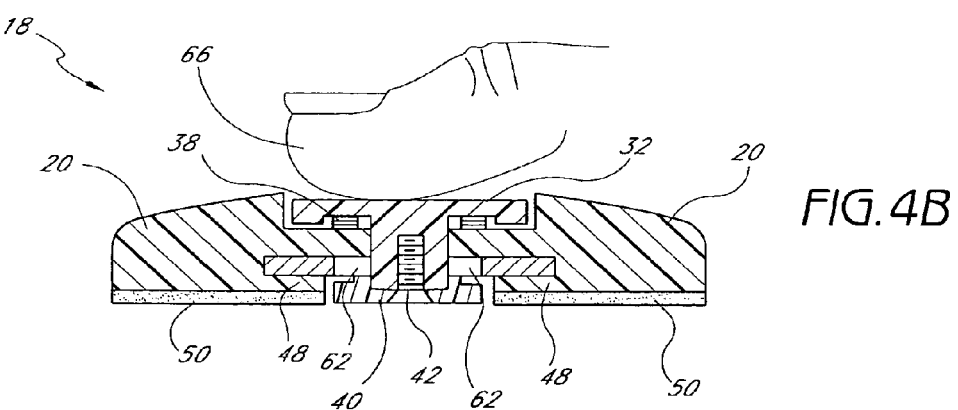

FIGS. 2B and 4A show the positively locked position of the adjustment assembly 30. The spring 38 normally urges (biases) the push-button top 32 up and away from the bottom of the chamber 27 and thereby captively urges the attached bushing 40 up into the selected pair of opposing notches 62a and 62b to retain the strut 12. The bushing 40 prevents the strut 12 from longitudinally moving relative to the wing assembly 18 while the bushing 40 is within a notch.

When a finger 66 applies downward pressure on the pushbutton top 32, the spring 38 is compressed and pushes the connected bushing 40 down out of the opposing notches 62a and 62b. With pressure still applied, the entire wing assembly 18 can be translated up or down the slot 46 (or vice-versa) until the pressure on the button 32 is removed and the bushing (stop member) 40 re-engages one of the pair of opposing notches 62a and 62b.

Figure 5:
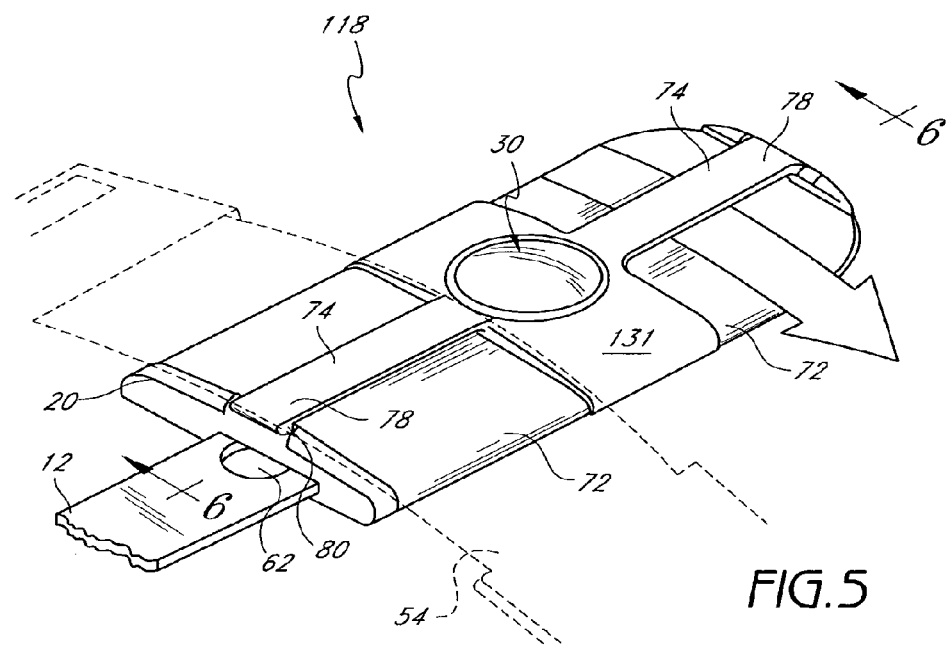
FIG. 5 is a perspective view of a second embodiment of an adjustable-length strut assembly.
Figure 6:
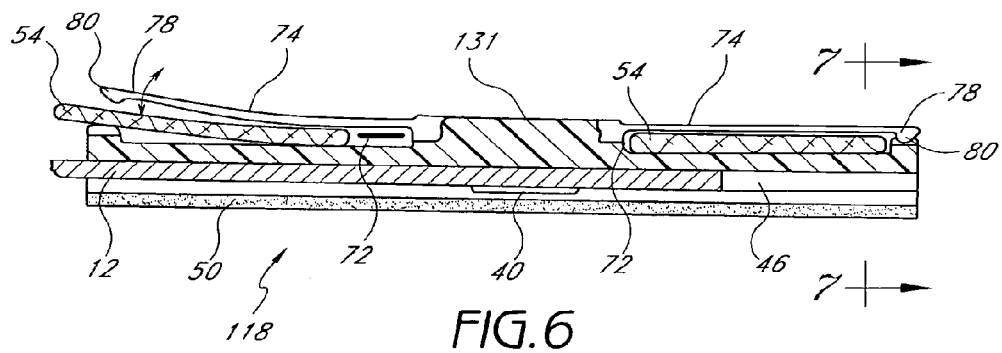
FIG. 6 is a cross-sectional view through the second embodiment of the adjustable-length strut assembly taken along line 6-6 of FIG. 5.
Figure 7:
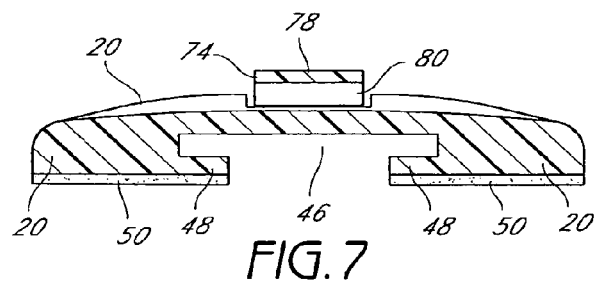
FIG. 7 is a cross-sectional view through the second embodiment of the adjustable-length strut assembly taken along line 7-7 of FIG. 6.

FIGS. 5, 6 and 7 depict a second embodiment of a wing assembly, generally designated 118 that telescopes in the exact manner just described with respect to the wing assembly 18. The second embodiment functions the same as the wing assembly 18 with respect to the adjustment of the length of the strut 12. The wing assembly 18 is provided with at least one strap-retaining channel 72 that runs transversely across the wing member 20. A strap-retaining loop 74 extends longitudinally outward from an adjustment assembly housing 131 that retains the adjustment assembly 30 across the entire width of the channel 72 and is flush with the top of the adjustment housing 131. The loops 74 may be formed of plastic, metal, or other suitable material that is resilient enough to be repeatedly bent and still spring downward to retain the strap 54. The adjustment assembly 30 is structured and functions in like manner to the adjustment assembly 30. Features and/or functions not discussed below with respect to the wing assembly 118 should be considered to be the same as those features and/or functions with respect to the wing assembly 18 unless noted to the contrary.

This configuration gives the wing assembly 118 a lower and sleeker profile that is less likely to get caught on obstructions during use. In addition, one end 78 of the retaining loop 74 is not connected to the wing body 20. The end 78 has a nub 80 to keep the strap 54 in place (FIGS. 6 and 7). The end 78 may also have a snap or other positive locking mechanism that is releasably engageable with the wing assembly 118. Referring to FIG. 6, the retaining loop 74 can be pivoted or bent up at the unconnected end 78 in order easily to slip in the strap 54. When the end 78 is released, the nub 80 ensures that the strap 54 will not slip out of the retaining channel 72. The arrow in FIG. 5 depicts where and how another strap may be placed.

Figure 8:
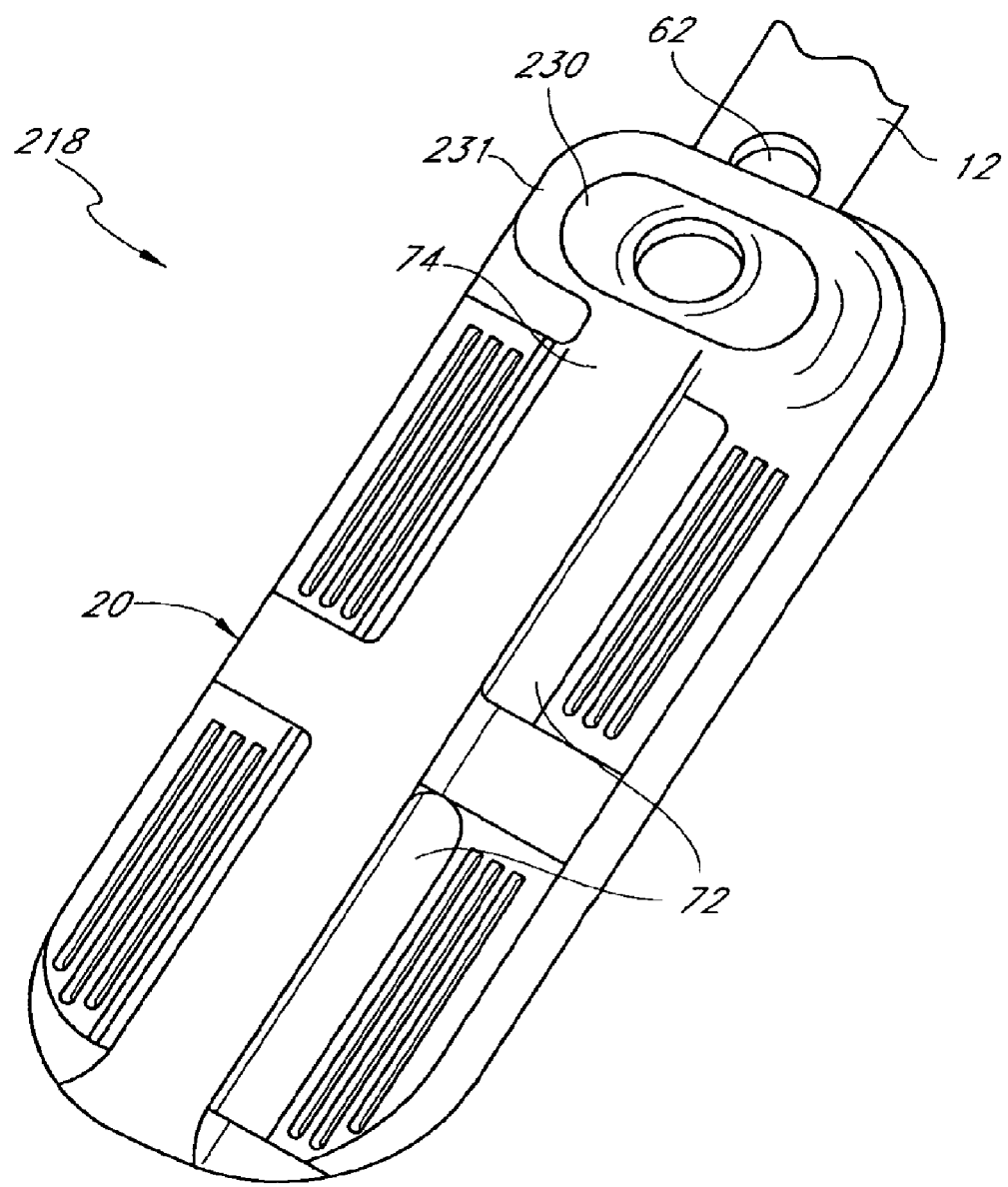
FIG. 8 is a perspective view of a third embodiment of an adjustable-length strut assembly.

FIG. 8 depicts a third embodiment of a wing assembly, generally designated 218. This third embodiment telescopes in the exact manner described with respect to the wing assemblies 18 and 118. Other features and/or functions not discussed below with respect to the wing assembly 218 should be considered to be the same as those features and/or functions with respect to the wing assemblies 18 and 118.

The wing assembly 218 is similar in design/appearance to the wing assembly 118. The wing assembly 218 includes a body or housing 20 having a unitary retaining loop 74 that defines two channels 72 for receipt of straps (54). The adjustment assembly 230 is oval rather than round to provide easier manipulation, and is situated at an end of the body 20, proximate the strut 12. The adjustment assembly 230 is surrounded by an adjustment housing 231.

Although the invention has been described in detail with reference to a preferred embodiment and an alternative embodiment, variations and modifications exist within the scope and spirit of the invention. Additional features of the invention will become apparent to those skilled in the art upon consideration of the detailed description of preferred embodiments exemplifying the best mode of carrying out the invention as presently perceived.

What is claimed is:

1. An orthopedic brace, comprising:
a first adjustable-length support;
a second adjustable-length support;
a hinge pivotably connecting the first and second supports; and
first and second adjustment mechanisms, wherein at least one of the first and second adjustment mechanisms comprises:
a strut;
a wing member slidable with respect to the strut in a direction substantially parallel to a longitudinal axis of the strut; and
a stop cooperating with the wing member, the stop contacting the strut to fix an amount of extension of the wing member with respect to the strut, the stop being biased by a resilient member that extends in a direction substantially perpendicular to the longitudinal axis of the strut.

2. The orthopedic brace of claim 1, wherein the stop comprises a shaft having at least a first flange extending therefrom.

3. The orthopedic brace of claim 2, wherein the strut includes at least two apertures spaced from one another along the longitudinal axis of the strut.

4. The orthopedic brace of claim 3, wherein the stop is biased toward a first position in which the flange engages one of the apertures in the strut, thus fixing an amount of extension of the wing member with respect to the strut.

5. The orthopedic brace of claim 4, wherein the stop is slidable to a second position in which the flange disengages one of the apertures, thus enabling the wing member to slide relative to the strut.

6. The brace of claim 2, wherein the stop further comprises a second flange spaced from the first flange along a longitudinal axis of the shaft.

7. The brace of claim 6, wherein a portion of the shaft between the flanges is axially translatable through an aperture in the wing member, the aperture having a width less than a diameter of either flange.

8. The brace of claim 6, wherein the coil spring is positioned between an underside of the second flange and a surface surrounding the aperture, such that the coil spring biases the stop toward a first position.

9. The brace of claim 8, wherein when the stop is in the first position the first flange engages one of a plurality of spaced notches on the strut to thereby fix a relative position of the wing member with respect to the strut.

10. The orthopedic brace of claim 1, wherein the resilient member comprises a coil spring.

11. The brace of claim 1, wherein the hinge is positioned between the first adjustment mechanism and the second adjustment mechanism.

12. The brace of claim 1, wherein the first adjustment mechanism comprises a first strut and the second adjustment mechanism comprises a second strut.

13. The brace of claim 12, wherein the hinge pivotably connects the first strut and the second strut.

14. The brace of claim 1, wherein the first adjustment mechanism is positioned on the first support.

15. The brace of claim 1, wherein the second adjustment mechanism is positioned on the second support.

16. An orthopedic brace, comprising:
a first adjustable-length support having a first adjustment mechanism and a longitudinal axis, wherein the first adjustment mechanism comprises a stop biased by a resilient member;
a second adjustable-length support having a second adjustment mechanism;

a hinge positioned between the first and second adjustment mechanisms; and wherein actuating the resilient member in a direction substantially perpendicular to the longitudinal axis of the first adjustable-length support releasably adjusts the position of the first adjustable-length support to a first position.

17. The brace of claim 16, wherein actuating the second adjustment mechanism releasably adjusts the position of the second adjustable-length support to a second position.

18. The brace of claim 16, wherein at least one of the first and second adjustment mechanisms comprises a strut and a wing member slidable with respect to the strut in a direction substantially parallel to a longitudinal axis of the strut.

19. The brace of claim 18, wherein at least one of the first and second adjustment mechanisms comprises a stop cooperating with the wing member, the stop contacting the strut to fix an amount of extension of the wing member with respect to the strut, the stop being biased by a resilient member in a direction substantially perpendicular to the longitudinal axis of the strut.

20. A method for bracing a limb, the method comprising: applying a brace to a limb, said brace having:

an adjustable-length support having a longitudinal axis; and an adjustment mechanism coupled to the adjustable-length support, wherein the adjustment mechanism comprises a stop and a resilient member that extends in a direction substantially perpendicular to the longitudinal axis of the adjustable-length support; and biasing the stop with the resilient member.

21. A method for assembling a brace for a limb, the method comprising:

pivotally connecting a first adjustable-length support having a longitudinal axis and a second adjustable-length support at a hinge;

positioning a wing member on the first adjustable-length support;

positioning a stop and a resilient member to cooperate with the wing member; and activating the resilient member in a direction substantially perpendicular to the longitudinal axis of the adjustable-length support to bias the stop, thereby setting a position of the wing member relative to the first adjustable-length support.

* * * * *